United States Patent [19]
Abraham et al.

[11] Patent Number: 5,827,888
[45] Date of Patent: Oct. 27, 1998

[54] PERINATAL TREATMENT OF A FETUS TO AVOID OXYGEN DEPRIVATION

[75] Inventors: Donald J. Abraham, Midlothian, Va.; Michael J. Gerber, Denver, Colo.

[73] Assignee: The Center For Innovative Technology, Herndon, Va.

[21] Appl. No.: 741,174

[22] Filed: Oct. 29, 1996

[51] Int. Cl.⁶ .................................................. A61K 31/19
[52] U.S. Cl. ........................................................... 514/563
[58] Field of Search .............................................. 514/563

[56] References Cited

U.S. PATENT DOCUMENTS

| | | | |
|---|---|---|---|
| 5,122,539 | 6/1992 | Abraham et al. | 514/563 |
| 5,290,803 | 3/1994 | Abraham et al. | 514/563 |
| 5,432,191 | 7/1995 | Abraham et al. | 514/563 |
| 5,525,630 | 6/1996 | Hoffman et al. | 514/563 |
| 5,648,375 | 7/1997 | Abraham | 514/421 |
| 5,677,330 | 10/1997 | Abraham et al. | 514/421 |

*Primary Examiner*—Rebecca Cook
*Attorney, Agent, or Firm*—Whitham, Curtis & Whitham

[57] ABSTRACT

A method of using allosteric hemoglobin modifier compounds which promote the release of oxygen to improve delivery of oxygen from the mother to the fetus and the release of oxygen to tissues from fetal hemoglobin in treatment of maternal and fetal related syndromes.

1 Claim, 3 Drawing Sheets

PERINATAL TREATMENT OF A FETUS TO AVOID OXYGEN DEPRIVATION

DESCRIPTION

BACKGROUND OF THE INVENTION

1. Field of the Invention

The invention is generally related to a new use of allosteric hemoglobin modifier compounds in treatments to improve the delivery and release of oxygen in maternal and fetal related syndromes.

2. Description of the Prior Art

The placenta is a remarkable fetal support system. It functions as the fetal lung and is responsible for all gas transfer from the mother to the fetus. Disruptions in the maternal circulation to the placenta and the fetal circulation during pregnancy can result in intrauterine growth retardation or fetal death. Such growth retardation may be a direct effect of hypoxia upon fetal tissues or caused by reduction in the supply of nutrients to the fetus. Histological characteristics used by prior investigations to describe placental insufficiency have been correlated to the consequences of fetal nutritional deprivation that result in chronic perinatal hypoxia.

As another related problem of interest, after delivery, premature newborns can suffer from inadequate oxygenation of tissues. That is to say, during pregnancy, high affinity fetal hemoglobin (Hbf) is essential for the fetus to "capture" an adequate quantity of oxygen from the mother's circulation via the placenta. However, this high affinity hemoglobin is not beneficial to the fetus after delivery. During normal labor and delivery, this does not cause concern. However, in situations of premature delivery, the accompanying neonatal respiratory distress syndrome (RDS), high affinity fetal hemoglobin is a liability to the neonate. These premature babies often require ventilator support or extracorporial membrane oxygenation (ECMO) therapy until the lungs mature. It would be desirable to improve the oxygen unloading characteristics of fetal hemoglobin in such circumstances in order to decrease the requirements for such ventilator support, ECMO or blood transfusion.

Prior to the present invention, there was no satisfactory treatment modality for increasing oxygen release to the fetus when the normal amount transferred from the mother does not occur due to a pathological reason, nor a satisfactory treatment for improving the oxygen unloading characteristics of fetal hemoglobin in premature newborns.

SUMMARY OF THE INVENTION

It is one object of this invention to provide a method for perinatal treatment of an oxygen deprived fetus or a potentially oxygen deprived fetus.

It is another object of this invention to provide a neonatal treatment for improving the oxygen unloading characteristics of fetal hemoglobin in premature newborn infants.

According to the invention, allosteric hemoglobin modifier compounds have been found which enhance the release and transfer of oxygen from the mother to the fetus and which increase unloading of oxygen to the tissues in newborn infants.

The invention has comprehensive applicability in both the practice of obstetrics and neonatology. The allosteric modifier compounds described herein can be used to address chronic or subacute uses in the treatment of intrauterine growth retardation during late stages of pregnancy. Additionally, the invention has acute applications. For instance, the allosteric modifier compounds described herein also can be administered to a mother to address fetal distress encountered during labor and delivery such as that associated with preclampsia, eclampsia, and complicated deliveries such as emergency C-section, breach delivery, cord strangulation, and so forth, to improve the clinical outcome of the fetus. Additionally, the allosteric compounds described are also beneficial when administered to the neonate (infant) after a premature delivery.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
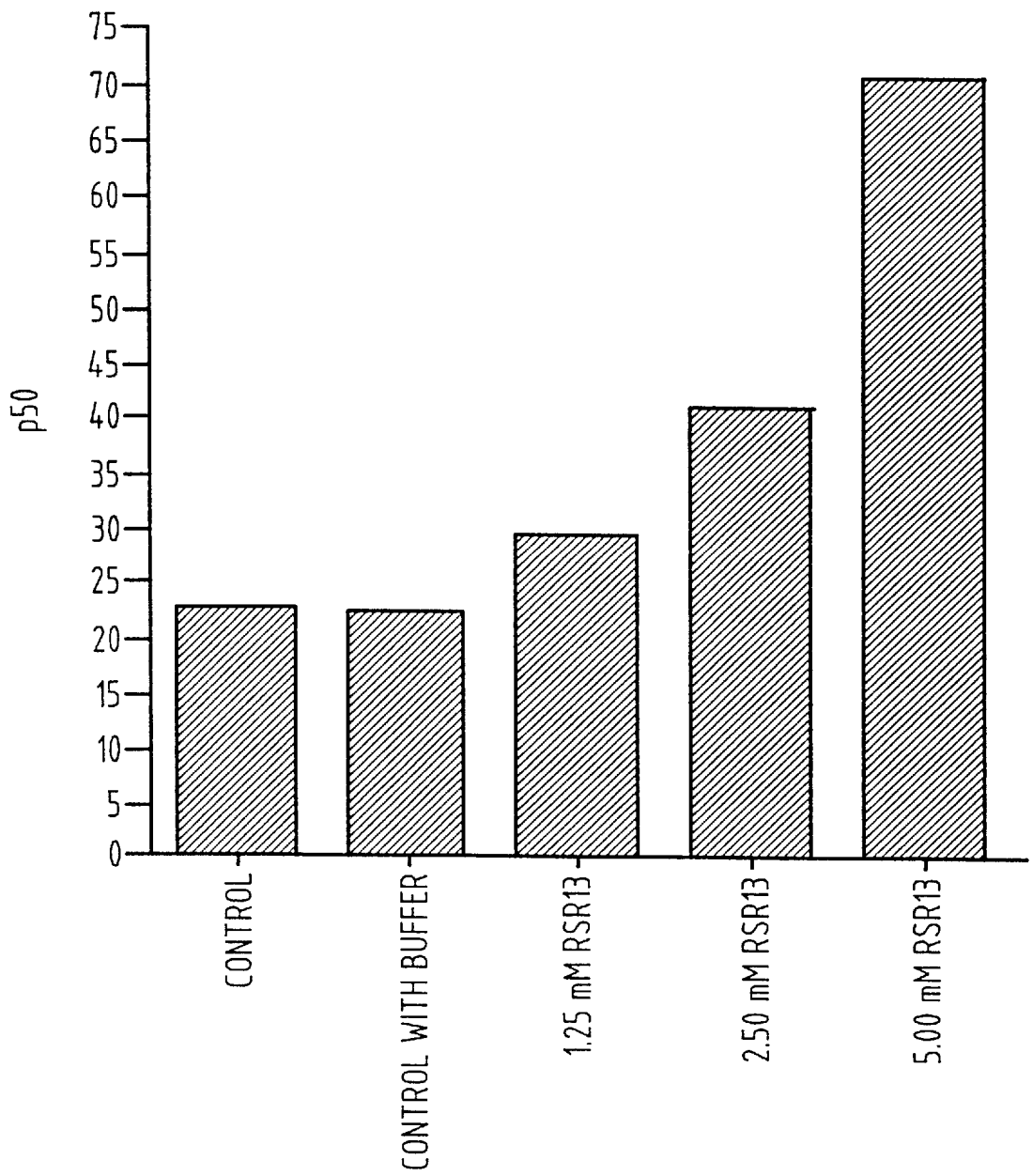
FIG. 1 is a bar chart showing the effect of increasing concentrations of an allosteric hemoglobin modifying compound (viz., RSR-13) used according to the invention on human cord blood in terms of the $P_{50}$ value measured for each sample.

The present invention relates to use of allosteric hemoglobin modifier compounds that decrease oxygen affinity of mammalian cord blood to facilitate improved delivery of oxygen in maternal and fetal related syndromes. Namely, a family of compounds has been found that causes right shifting of the oxygen dissociation curve of human cord blood towards a low oxygen affinity state ("T" or tense state). These compounds are useful for perinatal and neonatal applications related to the maternal and fetal syndromes. More specifically, these compounds are useful: (a) to deliver more oxygen to the maternal and fetal tissues; (b) to improve the availability of oxygen to the placenta and subsequently to the fetus in IUGR (i.e., Intra Uterine Growth Retardation) pregnancy; (c) to improve the course of maternal syndrome by supplying critically-needed oxygen to the maternal tissues in the Preclampsia pregnancy; and/or (d) to improve the oxygen unloading characteristics of fetal hemoglobin in neonates after a premature delivery. The meaning of the "low oxygen affnity" and "right shifted" terminology used herein will be understood by one of skill in the art, such as by reference to the background teachings in U.S. Pat. No. 5,290,803 (Abraham et al.).

EXPERIMENTAL

An experimental study was conducted to investigate the effect of 2-[4- ((((3,5-dimethylphenyl)amino)carbonyl) methyl)phenoxy]-2-methyl propionic acid, identified herein as compound "RSR-13" for short, on the oxygen affinity of human cord blood in vitro using multipoint tonometry method.

Freshly drawn, human cord blood was obtained from the Labor and Delivery Department of the Medical College of Virginia Hospitals, Richmond, Va. U.S.A. The blood samples were collected in heparinized tubes and stored over ice until the analysis. The effect of RSR-13 on the oxygen affinity of human cord blood was measured in vitro at three different concentration levels (viz., 1.25, 2.5 and 5.0 mM) of the active compound (i.e., RSR-13) using the multipoint tonometry method.

As to the preparation of the control and test samples, a 50 mM stock solution ofRSR-13 was prepared in 50 MMHEPES buffer. The 50 M HEPES buffer solution was (N-[2-hydroxyethyl]piperizine-N'-[2-ethane sulfonic acid]) and EDTA (ethylenediaminetetraacetic acid) at pH 7.41. The control sample was prepared by mixing 1800 μl of human cord blood with 200 μl of HEPES buffer. The 1.25 mMRSR-13 test solution was prepared by mixing 1950,μl of human cord blood with 50 μl of 50 mM RSR-13 stock solution. The 2.50 mM RSR- 13 test solution was prepared by mixing 1900 μl of human cord blood with 50 μl of 100 mM RSR-13 stock solution. The 5.0 mM RSR-13 test solution was prepared by mixing 1800 μl of human cord blood with 200 μl of 50 mM RSR-13 stock solution.

All of these samples were incubated in tonometers (model IL 237, Instrument Laboratories, Lexington, Mass.) for 1 hour at 37° C. and allowed to equilibrate at three different concentrations of oxygen mixtures (20, 40 and 60%). At each concentration of oxygen a sample was removed via syringe and injected into an IL BG3 and BGE blood gas analyzer and model IL 482 co-oximeter (Instrument Laboratories, Lexington, Mass.) to obtain the oxygen saturation values ($pO_2$).

Measured values for $pO_2$ and $satO_2 26$ (saturation of oxygen at 26 mm Hg) at each oxygen saturation point were then used to determine $P_{50}$ (i.e., the partial pressure at which 50% of the hemoglobin molecule is saturated with oxygen), $n_{50}$ (i.e., the Hill Coefficient at 50% hemoglobin saturation), and calculated $satO_2$-26 using linear regression analysis.

The other hemoglobin (Hb) parameters such as total hemoglobin (tHb) concentration, met Hb (hemoglobin which does not bind iron) were calculated using the spectral extinction coefficients via co-oximeter and pH of each sample was measured by the blood gas analyzer.

The $P_{50}, \Delta P_{50}$, (i.e., $P_{50}$ of test sample minus $P_{50}$ of control with buffer alone), $n_{50}$, and percentage oxygen saturation at 26 mm Hg (sat. 26%) results are summarized in Table 1.

TABLE 1

| sample | $P_{50}$ | $\Delta P_{50}$ | $n_{50}$ | sat 26% |
| --- | --- | --- | --- | --- |
| control | 23 | — | 3.2 | 61 |
| control + buffer | 22 | 0.00 | 3.1 | 62 |
| 1.25 mM RSR-13 | 29 | 7.12 | 2.1 | 44 |
| 2.50 mM RSR-13 | 41 | 18.77 | 1.8 | 30 |
| 5.0 mM RSR-13 | 70 | 48.26 | 1.6 | 17 |

Figure 2:
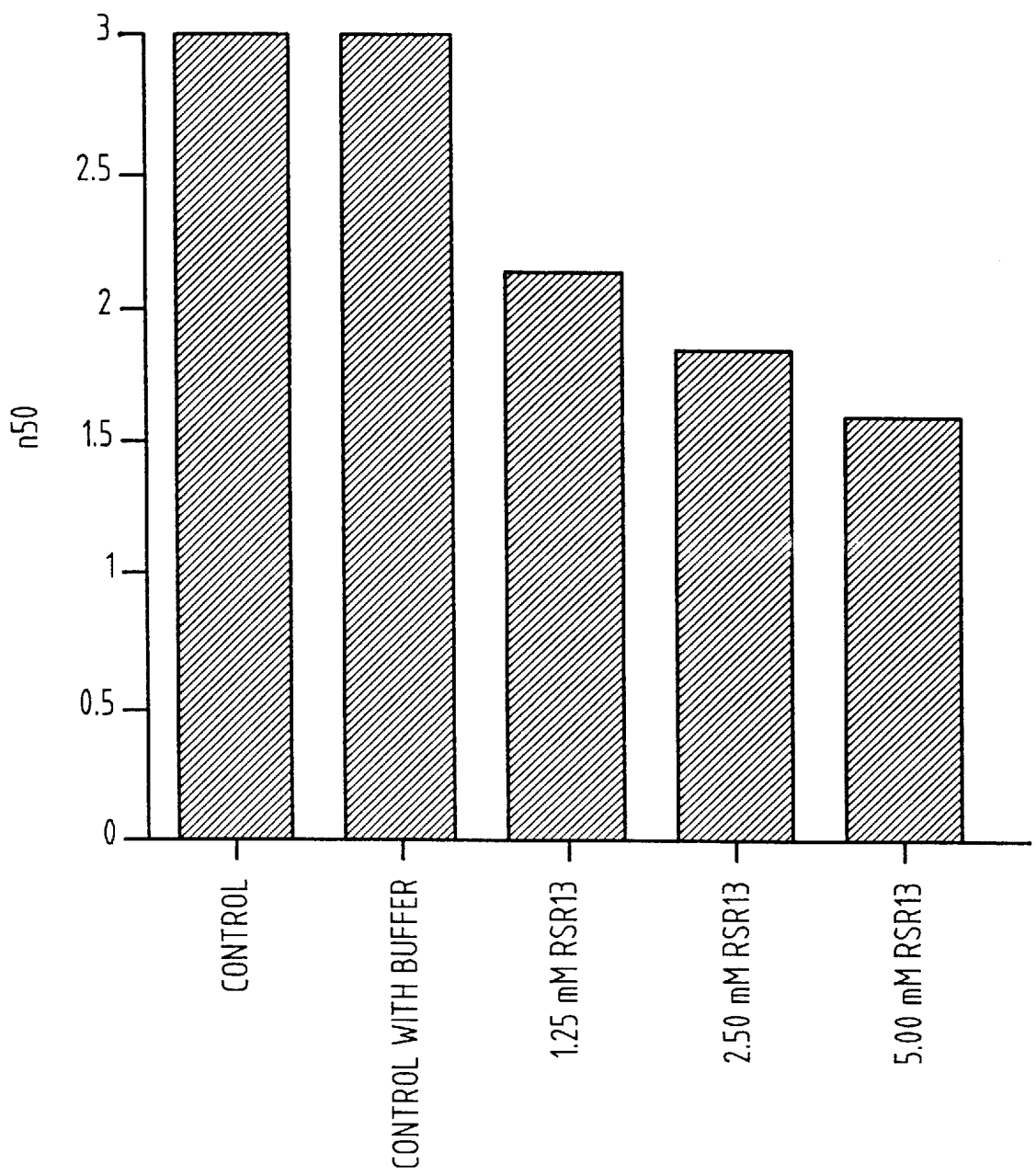
FIG. 2 is a bar chart showing the effect of increasing concentrations of an allosteric hemoglobin modifying compound (viz., RSR-13) according to the invention on human cord blood in terms of the Hill Coefficient $n_{50}$ value measured for each sample.
Figure 3:
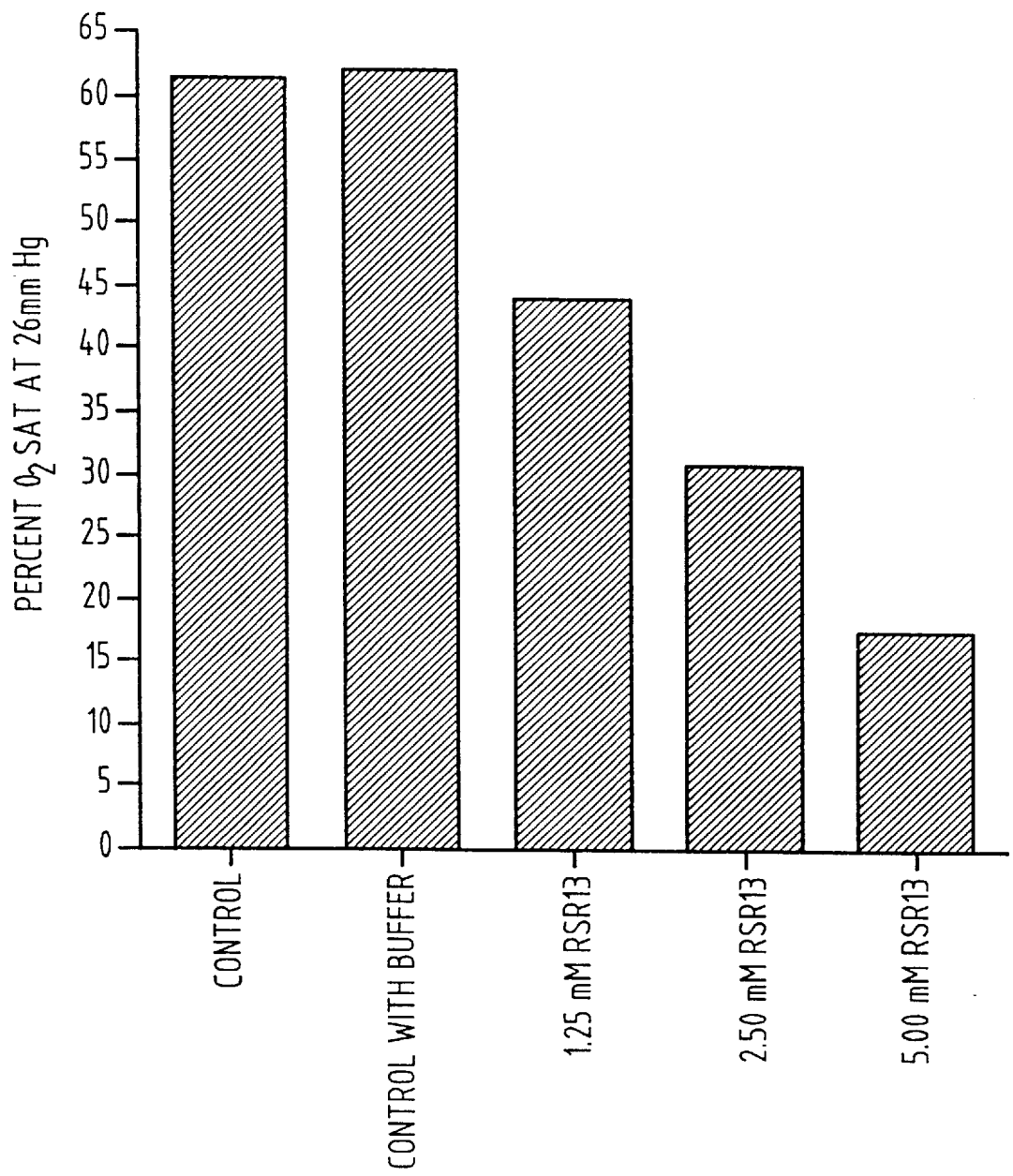
FIG. 3 is a bar chart showing the effect of increasing concentrations of an allosteric hemoglobin modifying compound (viz., RSR-13) according to the invention on human cord blood in terms of the oxygen % saturation value measured for each sample (saturation at 26 mm Hg).

The results are graphically summarized in the bar graphs shown in FIGS. 1—3. FIG. 1 compares the dose-response changes in $P_{50}$ of human cord blood. FIG. 2 shows the changes in $n_{50}$ with respect to RSR-13 concentration variation. FIG. 3 represents the changes in percent oxygen saturation at 26 mm Hg with increasing concentration of RSR-13.

Considering the results, it should be noted that the $P_{50}$ values of the control and the control with HEPES buffer (22.5 and 22, respectively) were much lower than that of normal human whole blood (i.e., 27) at physiological conditions. This is because the fetal hemoglobin (HbF) is the predominant hemoglobin in the fetus and the newborn. The fetal hemoglobin protein (HbF) has two α chains similar to normal adult hemoglobin (HbA), but two γ chains instead of two β chains that are normally observed in HbA. These two γ chains are each quite different from the two β chains in HbA (i.e., there are several differences in amino acids between the proteins in the γ chains in Hbf and β chains in HbA). Fetal hemoglobin HbF appears by the 5th week of gestation and persists for several months after birth. The decline in HbF synthesis as a function of gestational age is shown at the end of this report. HbF has an increased affinity for oxygen and as a result the oxygen dissociation curve is left shifted as compared to normal hemoglobin HbA. The treatment of the cord blood at the 1.25, 2.5, and 5.0 mM RSRS-13 concentrations increased the P50 value by 7.12, 18.77, and 48.26, respectively. An x-ray crystallographic analysis of the deoxy HbA-RSR13 complex exhibited a pair of symmetry related binding sites in the central water cavity of hemoglobin. It was noteworthy that even though there are no β chains in HbF, that RSR-13 still shifted the oxygen dissociation curve of human cord blood to the right and stabilized the T (tense) state of the fetal hemoglobin.

A comparison of the Hill coefficient $n_{50}$ values of the control sample and the RSR- 13 treated samples clearly indicates that binding of RSR- 13 to cord blood has a negative cooperativity since the $n_{50}$ value dropped from 3.16 (control) to 2.1, 1.8, and 1.6 at 1.25, 2.5, and 5.0 mM RSR-13 concentrations, respectively.

FIG. 3 shows a similar comparison of percentage saturation at 26 mm Hg between RSR-13 treated samples and the control sample indicates that RSR-13 definitely delivers more oxygen, as indicated by the lower sat 26 values, than the control whole blood.

The results demonstrated that RSR-13 shifted the oxygen dissociation curve of human cord blood to the right at all positive concentrations levels investigated. The results indicate that RSR-13 will be useful in improving the delivery of oxygen to the fetus from the mother because it modifies the oxygen affinity of human cord blood in such a way that should, in turn, result in increased placental oxygen transfer at low oxygen tension levels. The resulting enhanced tissue oxygenation of fetuses will provide them an oxygen-rich environment. Moreover, the results indicate that RSR-13 will be useful in improving the release of oxygen from HbF in the fetus/newborn to its tissues.

Thus, RSR-13 should be useful in treating oxygen deficiency related maternal syndromes such as chronic use to treat intrauterine growth retardation resulting from inadequate fetal oxygenation occurring during late stage pregnancy. However, RSR-13 also should be effective for acute uses involving fetal distress associated with pre-eclampsia or eclampsia. Specifically, when there is evidence of fetal distress, the physician can administer RSR- 13 to the mother to temporarily improve oxygen unloading from the maternal circulation to the fetal circulation. Equally important, RSR-13 can be expected to cross the placenta and impact the fetal hemoglobin directly in the manner described above. This same approach can be undertaken in situations involving fetal distress associated emergency C-section, breach delivery, cord strangulation, or other hypoxic maladies that occur in the practice of obstetrics. Similarly, RSR-13 should be useful in neonatology to improve the oxygen unloading characteristics of fetal hemoglobin in newborn infants to reduce requirements for require mechanical ventilation, ECMO, or blood transfusion. RSR-13 should prove beneficial in this situation by decreasing oxygen-hemoglobin affinity of the "abnormal" fetal hemoglobin. This approach should also have other application in other delivery complications such as neonatal meconium aspiration and will help to reduce the requirement for blood transfusion.

While the experiments were conducted with RSR-13, other allosteric hemoglobin modifier compounds which right-shift the oxygen dissociation curve and cause hemoglobin to bind oxygen less tightly may also be used within the practice of this invention. In addition, it should be understood that RSR-13 is a representative compound for the class of allosteric hemoglobin modifier compounds having the general structural formula:

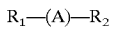

where $R_1$ and $R_2$ each are a substituted or unsubstituted aromatic or heteroaromatic compound, or a substituted or unsubstituted alkyl or heteroalkyl ring compound, or a substituted or unsubstituted phthalimide compound, where $R_1$ and $R_2$ may be the same or different, where A is a chemical bridge which includes 2–4 chemical moieties bonded together between $R_1$ and $R_2$, wherein said chemical moieties in A are selected from the group consisting of CO, $CH_2$, O,S,$SO_2$,NH,$NR_3$ where $R_3$ is a $C_{1-6}$ alkyl group, $NR_4$ where $R_4$ includes two carbonyls as part of a phthalimide compound formed with $R_1$ and $R_2$, $CH_2$, CH, and C, and wherein at least one of $R_1$ and $R_2$ is substituted with a compound having the chemical formula:

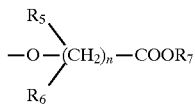

where n is zero to five, where $R_5$ and $R_6$ are selected from the group consisting of hydrogen, halogen, substituted or unsubstituted $C_{1-2}$ alkyl groups, substituted and unsubstituted aromatic or heteroaromatic groups, and these moieties may be the same or different, or alkyl moieties of part of an aliphatic ring connecting $R_5$ and $R_6$, where $R_7$ is a hydrogen, halogen, salt cation, metal or substituted or unsubstituted $C_{1-6}$ alkyl group.

A number of allosteric effectors covered by the above general formula bind to HbA similar to RSR-13, and, consequently, it can be deduced that all of them would possess similar capability to shift the oxygen dissociation curve of cord blood to the right. Thus, any compound fitting this description should be useful in the practice of this invention due to their allosteric activity with the hemoglobin molecule. Synthesis of the allosteric hemoglobin modifier compounds of the present invention is described in detail in U.S. Pat. Nos. 5,290,803, 5,122,539, and U.S. Pat. No. 5,432,191, and each of these documents is incorporated herein by reference. It is thought that the compounds of the above formula enhance tissue oxygenation by the release of molecular oxygen from erththrocytes by altering the oxygen affinity of hemoglobin.

The dose of the allosteric hemoglobin modifier compound given to a mother (human or animal) of the fetus needing treatment for oxygen deprivation, or to a premature newborn infant needing increased unloading of oxygen from HbF to the tissues, will depend on a number factors including the route of delivery (e.g., oral, intravenous i.v.,intraperitoned i.p., aerosol spray), age of patient, etc.

In the experiment noted above, the RSR-13 compound was dispersed in HEPES buffer. However, it should be understood that any vehicle in which RSR-13 or other allosteric hemoglobin modifier compounds can be dissolved or dispersed could be used within the practice of this invention. Suitable examples include oils, fat emulsions, suspensions, liposomes, lipid vesicles, etc., where the terms lipid, phospholipid, and fat can be used interchangeably.

While the invention has been described in terms of its preferred embodiments, those skilled in the art will recognize that the invention can be practiced with modification within the spirit and scope of the appended claims.

We claim:

1. A method for perinatal treatment of a fetus to avoid oxygen deprivation, comprising the step of administering to a mother of a fetus in need thereof a sufficient quantity of 2-[4-((((3,5-dimethylphenyl)amino)carbonyl)methyl) phenoxy]-2-methyl propionic acid to increase release of oxygen from said mother to said fetus.

* * * * *